United States Patent [19]

Sak et al.

[11] Patent Number: 4,510,621
[45] Date of Patent: Apr. 9, 1985

[54] SELF-SEALING POUCH FOR FORMING ADHESIVE-TO-ADHESIVE SEAL

[75] Inventors: Dennis A. Sak, Hinsdale; Thomas Mestetsky, St. Charles, both of Ill.

[73] Assignee: Arvey Corporation, Chicago, Ill.

[21] Appl. No.: 509,396

[22] Filed: Jun. 30, 1983

[51] Int. Cl.³ .................. B65D 33/20; B65D 77/12
[52] U.S. Cl. ................................. 383/89; 206/438; 206/484; 206/807; 206/813; 229/485 A; 229/80
[58] Field of Search ............... 206/438, 439, 484, 813, 206/807, 363; 229/48 SA, 48 SB, 80, 79, 81; 383/89

[56] References Cited

U.S. PATENT DOCUMENTS

| | | | |
|---|---|---|---|
| 2,215,989 | 9/1940 | Wolf | 229/48 SA |
| 3,507,444 | 4/1970 | Werby | 229/68 |
| 3,625,351 | 12/1971 | Eisenberg | 206/484 |
| 3,675,844 | 7/1972 | Sorrell | 229/80 |
| 3,819,106 | 4/1972 | Schuster | 229/80 |

Primary Examiner—William T. Dixson, Jr.
Attorney, Agent, or Firm—Dressler, Goldsmith, Shore, Sutker & Milnamow, Ltd.

[57] ABSTRACT

A disposable, self-sealing pouch is disclosed which is readily adaptable for use for sterilization, sterility maintenance, disposal of contaminated items, and like medical applications. The pouch includes first and second coextensive pouch webs which are marginally joined together to define the interior of the pouch. The first pouch web defines a transversely extending access opening slit through which articles may be inserted into the pouch. In order to effect closing and sealing of the access opening slit, the pouch includes adhesive means provided on the first pouch web on opposite sides of the access opening slit. By this construction, the pouch may be easily and securely sealed by folding the pouch onto itself so that the adhesive means is brought into confronting relation with itself, thus forming an adhesive-to-adhesive of the access opening slit.

17 Claims, 9 Drawing Figures

U.S. Patent    Apr. 9, 1985    4,510,621
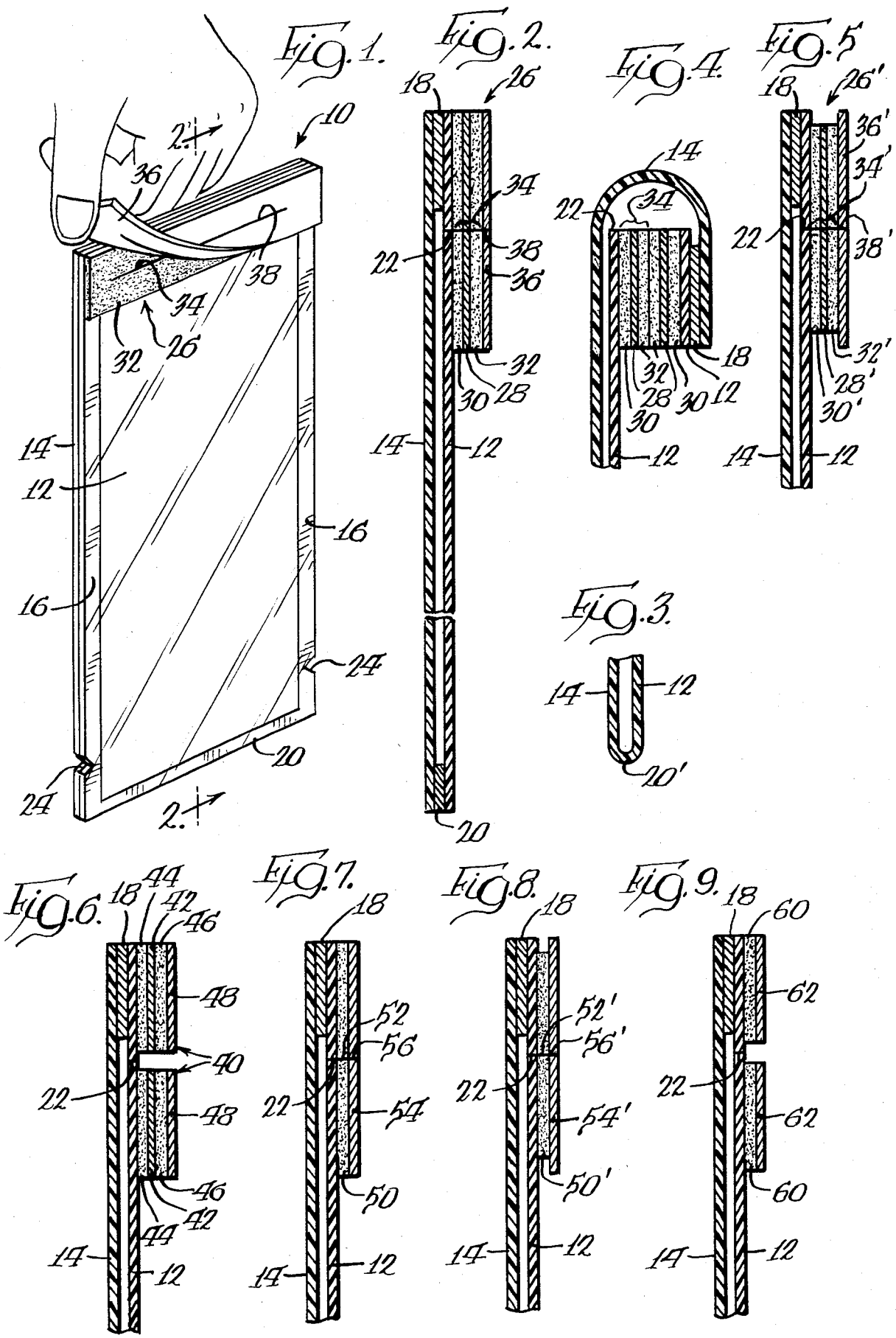

4,510,621

SELF-SEALING POUCH FOR FORMING ADHESIVE-TO-ADHESIVE SEAL

CROSS-REFERENCE TO RELATED APPLICATION

The present disclosure is related to U.S. application Ser. No. 509,861, filed June 30, 1983.

TECHNICAL FIELD

The present invention relates generally to self-sealing, disposable pouch constructions, and more particularly to an improved self-seal pouch having an access opening slit flanked by pressure-sensitive adhesive for forming an adhesive-to-adhesive closing seal.

BACKGROUND OF THE INVENTION

In the health care industry, it is routinely necessary to sterilize, and maintain in a sterile condition, very large numbers of medical articles such as surgical instruments and the like. To this end, self-sealing pouches have been developed which are adapted to receive a medical article and be sealed, with the pouch and its contents then being subjected to sterilization such as by autoclaving, or by ethylene oxide gas or radiation exposure. The contents of the pouch are then maintained in a sterile condition until ready for use. Commonly-assigned U.S. Pat. No. 4,276,682, to Sibrava et al., discloses one such sterilizable pouch construction which has proven to be highly commercially successful.

In a similar regard, pouches and bags (sometimes referred to as dust covers) are also known which are suited for "sterility maintenance." Such pouches are usually adapted to receive an article after it has been sterilized (frequently while the article is still sealed within its sterilization pouch), and after sealing maintain the article in a sterile condition. Still other types of pouches are known which are suited for disposal of contaminated items.

It will be recognized that depending upon the intended use of a pouch, it is frequently important that the closing seal formed in the pouch after an article has been inserted therein be of high integrity, and prevent passage of contaminants. Therefore, it is not only desirable that a self-sealing pouch be configured to facilitate proper sealing (usually effected by hand), but it is frequently further desirable that the seal formed at the access to the interior of the pouch be secure as possible.

As is known in the art, the materials from which a pouch is fabricated must be appropriately selected for the intended use of the pouch. For example, some types of materials are suited for some sterilization processes, but not others. Additionally, pouch materials must be selected to assure their compatability with the adhesive employed for sealing the pouch, bearing in mind that the adhesive must be selected in accordance with government-established standards if the pouch is to be used for medically-related purposes.

In the past, these design parameters have acted to limit the flexibility of selection of pouch materials for self-sealing pouches. To assure sufficient useful shelf life for a pouch, pouch materials have been selected which, over time, do not lose their compatability with approved adhesives. For example, polyethylene plastic film must be corona discharge treated to assure its compatability with currently used approved adhesives, but this treatment deteriorates over time so shelf life is undesirably limited if the closing seal of the pouch is effected between the pouch's adhesive and its treated polyethylene film web.

Therefore, it is extremely desirable to provide a self-sealing pouch construction wherein an adhesive-to-adhesive closing seal is formed. In this way, the adhesive can be applied to the pouch during fabrication at a time when any required treatment of the pouch's web(s) has been recently effected to assure the integrity of the adhesive/web interface, with the adhesive-to-adhesive closing seal not being dependent upon the freshness of any web treatment. This permits the pouch web material to be selected without concern of excessive deterioration of its adhesive compatability over time.

In keeping with the above desired goals, the present invention entails a self-sealing pouch which is economically fabricated and very easy to use, and which is configured to provide a very secure adhesive-to-adhesive closing seal at the access opening of the pouch.

SUMMARY OF THE INVENTION

The self-sealing pouch of the present invention can be readily fabricated from different types of materials so that the pouch is suited for sterilization, sterility maintenance, and other types of uses. Significantly, the present pouch includes an access opening which is flanked by pressure-sensitive adhesive so that when the pouch is folded onto itself preferably generally at the access opening, a very secure adhesive-to-adhesive seal of the opening is formed.

In the preferred embodiment of the present pouch, the pouch comprises first and second, generally rectangular, coextensive pouch webs which are joined together along all marginal edge portions thereof to define the interior of the pouch. The pouch webs preferably each comprise plastic film, although the webs may be made of differing materials. The pouch webs are marginally joined together such as by heat sealing. If desired, the pouch webs can be formed from a single piece of web material folded onto itself to provide the coextensive webs, with the webs thus being joined at the fold of the piece of material, and further marginally joined such as by heat sealing.

The first pouch web defines an access opening slit generally adjacent one end thereof for providing access to the interior of the pouch. The access opening slit extends generally transversely of the pouch, and preferably extends less than the distance between the heat seals or like means joining together the opposite lateral marginal edge portions of the first and second pouch webs.

Significantly, the present pouch further includes a pressure-sensitive adhesive structure provided on the first pouch web on opposite sides of the pouch's access opening slit such that the access slit is flanked by pressure-sensitive adhesive. By this construction, the access slit can be closed and sealed by folding the pouch onto itself to bring the pressure-sensitive adhesive into confronting relation with itself to thus form an adhesive-to-adhesive seal at the access opening slit. Notably, the access opening slit in the first pouch web provides a "natural" folding line for the pouch construction. This facilitates convenient use of the pouch, and permits the pouch to be manufactured either with or without scoring or like means for forming a fold line. The adhesive-to-adhesive seal formed is highly secure, and is not dependent upon the compatability of the adhesive with the pouch webs. Additionally, the closing seal is formed between like pouch web materials to avoid problems of uneven shrinkage which can sometimes occur attendant to steam sterilization of self-sealing pouches having closing seals formed between differing materials.

In one embodiment of the present pouch, closing of the access opening slit is effected by means of a laminate adhesive structure. This construction comprises a preferably paper, adhesive carrier member having first and second pressure-sensitive adhesive layers on opposite expansive surfaces thereof. The laminate adhesive structure defines an opening aligned with the access opening of the pouch, with the adhesive structure affixed to the first pouch web with the first adhesive layer during manufacture of the pouch so that any special treatment (such as corona discharge) of the first pouch web is fresh to assure the integrity of the interface between the adhesive and the web. The second adhesive layer, which extends along the opposite sides of the transversely extending access slit, can then be employed for effecting the adhesive-to-adhesive closing seal of the access slit. Removable release paper is preferably provided on the second adhesive layer to maintain its freshness, with the release paper defining a further opening aligned with the access slit so that an article may be inserted into the pouch before the release paper is removed.

Alternate constructions of the present pouch are also disclosed wherein the adhesive provided on opposite sides of the pouch's access opening slit is provided in the form of a pair of adhesive strips respectively positioned on the first pouch web on opposite sides of the access opening slit. Each of these two adhesive strips may comprise a laminate adhesive structure including an adhesive carrier member and first and second layers of adhesive, or each may comprise a single layer of adhesive.

Notably, the use of a laminate adhesive structure for sealing the present pouch facilitates tamper-indication. The laminate adhesive structure is preferably configured such that the effective adhesive strength of the first and second adhesive layers of the structure is greater than the internal or cohesive strength of the adhesive carrier member. By this arrangement, any effort to reopen the access opening slit of the pouch results in delamination of the adhesive structure by rupture of the adhesive carrier member, thus clearly indicating tampering.

In order to facilitate convenient removal of the contents of the present pouch, the pouch preferably comprises a tear notch defined by the joined-together first and second pouch webs on at least one marginal edge of the pouch intermediate the ends thereof, and preferably closer to the end of the pouch opposite its sealing arrangement. The pouch can easily be opened by merely tearing it at the tear notch, which then results in propagation of the tear across the first and second pouch webs. To further facilitate convenient use of the present pouch, the removable release paper provided on its sealing adhesive can be dimensioned larger than the adhesive, thus permitting the release paper to be easily grasped and removed when the pouch is ready to be sealed.

Numerous other advantages and features of the present invention will become readily apparent from the following detailed description, the accompanying drawings, and the appended claims.

BRIEF DESCRIPTION OF THE DRAWINGS

FIG. 1 is a perspective view of a self-sealing pouch embodying the principles of the present invention;

FIG. 2 is an enlarged cross-sectional view taken generally along lines 2—2 of FIG. 1;

FIG. 3 is a cross-sectional view which illustrates a modified construction for the present pouch;

FIG. 4 is a cross-sectional view which illustrates the pouch of FIGS. 1 and 2 after it has been folded onto itself for sealing;

FIG. 5 is a cross-sectional view similar to FIG. 2 illustrating a further modification of the pouch illustrated in FIGS. 1 and 2;

FIG. 6 is a cross-sectional view illustrating an alternate embodiment of the present invention;

FIG. 7 is a cross-sectional view similar to FIG. 2 illustrating a further alternate embodiment of the present invention;

FIG. 8 is a cross-sectional view similar to FIG. 7 illustrating a modification of the embodiment of the present pouch illustrated in FIG. 7; and FIG. 9 is a cross-sectional view similar to FIG. 7 illustrating a further embodiment of the present invention.

DETAILED DESCRIPTION

While the present invention is susceptible of embodiment in various forms, there is shown in the drawings and will hereinafter be described various embodiments of the invention, with the understanding that the present disclosure is to be considered as an exemplification of the invention, and is not intended to limit the invention to the specific embodiments illustrated.

It should be noted that for purposes of clarity of this disclosure, the constructions of the present invention illustrated in the accompanying drawings have not been drawn to scale. As will be recognized by those familiar with the art, the various components of the present pouch structure ordinarily have thicknesses on the order of a fraction of a mil to several mils. As will be further recognized, pouches formed in accordance with the teachings herein can be made in many different sizes.

With reference now to FIGS. 1 and 2, therein is illustrated a self-sealing pouch 10 embodying the principles of the present invention. The present pouch includes first and second coextensive pouch webs 12 and 14, which are preferably generally rectangular and preferably of the same dimensions. The pouch webs 12 and 14 are joined together along all of their marginal edge portions to define the interior of pouch 10 within which medical articles or the like can be inserted.

The method by which the webs of the present pouch are sealingly joined together can be appropriately effected in a number of ways. Depending upon the materials from which pouch webs 12 and 14 are formed, which are ordinarily selected with consideration of the intended pouch use, the present pouch may be formed either with or without the use of one or more adhesive layers between the pouch webs for sealingly joining the webs together. Such adhesive layers can be coated to one or both of the pouch webs before the webs are joined, as is well known in the art. In this regard, the joining of the webs can be effected with heat sealing, either in conjunction with adhesive material, or by direct heat-sealing of the pouch webs together without the use of adhesive. These various techniques are known, and the present pouch is readily adaptable for formation using a wide variety of techniques and materials.

In one presently preferred embodiment of the present pouch, each of the first and second pouch webs 12 and 14 comprises polyolefinic transparent plastic film such as polyethylene, polypropylene or blends thereof. Other plastic films may also be employed, such as polyethylene terephthalate, nylon, or a laminate of polyethylene terephthalate and polypropylene. Alternately, paper or paper-like material can be employed for one or both of pouch webs 12 and 14, such as surgical kraft paper, or synthetic or artificial paper-like material such as those comprising spun, bonded plastic fibers and the like. As noted, material selection is ordinarily dependent upon the intended use of the pouch since, for example, some materials are better suited than others for certain sterilization processes. Because the present pouch arrangement is readily adaptable for use with all types of sterilization processes including gas, radiation and steam sterilization, as well as being adaptable for non-sterilization use (such as sterility maintenance or disposal of contaminated articles), the materials for the webs of the pouch can be appropriately selected for the intended use.

The marginal edge portions of first and second pouch webs 12 and 14 are joined together along side edge seals 16, end seal 18 (FIG. 2), and end seal 20 by heat-sealing. Alternately, the first and second pouch webs may be formed from a single piece of web material, and thus joined together at one end edge thereof at the fold 20' of the single piece of web material, as illustrated in FIG. 3. In such a construction, the remaining marginal edge portions of the first and second webs are joined together such as by heat sealing at seals 16 and 18.

In order to gain access to the interior of pouch 10 for insertion of articles therein, first pouch web 12 defines a preferably transversely extending access opening slit 22. The access opening slit preferably extends transversely of the pouch a distance less than the distance between side edge seals 16, and is preferably positioned just inwardly of end seal 18. As will be further described, the present pouch is adapted to be folded onto itself preferably generally about access slit 34, with the access slit providing a "natural" folding line for very conveniently effecting a seal thereof. If desired, a "pre-fold" for the pouch can be formed during its manufacture by folding the pouch at access slit 34 (or along a line spaced from the access slit if desired), and lightly heat sealing. As will be recognized, access slit 34 may alternately comprise a slot-like opening.

The present pouch is preferably configured so as to deter opening of access slit 22 after it has been sealed. Therefore, in order to gain access to the interior of pouch 10 for removal of its contents, means are preferably provided apart from the access slit 22 for opening the pouch. The opening means preferably comprises one or more tear notches 24 defined by the joined together marginal side edge portions of the first and second pouch webs 12 and 14. The provision of one or more tear notches 24 facilitates convenient opening of the pouch after it has been sealed since the pouch can be easily gripped and torn at one of the tear notches 24, with the tear then propagating across the first and second pouch webs 12 and 14.

As discussed above, the access opening slit 22 of the pouch is adapted to be closed and sealed with an adhesive-to-adhesive seal formed between adhesive areas disposed along respective opposite sides of the access slit. As best illustrated in FIG. 2, this embodiment of the present pouch includes a laminate adhesive structure 26 for effecting sealing of access slit 22. The adhesive structure 26 comprises an adhesive carrier member 28, preferably comprising paper, and first and second pressure-sensitive adhesive layers 30 and 32 disposed on respective opposite sides of the carrier member 28. Adhesive structure 26 defines an opening 34 in alignment with access opening slit 22, thus flanking the access slit with adhesive. The access slit 22 is preferably disposed generally centrally of the adhesive structure 26, with the adhesive structure positioned about the access slit.

A removable release paper 36 is preferably provided on the second adhesive layer 32 for maintaining the freshness thereof, with the release paper 36 defining a further opening 38 aligned with opening 34 and access opening slit 22. By this construction, the adhesive structure 26 may comprise a single strip having release paper 36 affixed to its second adhesive layer 32, with this arrangement applied to first pouch web 12 during manufacture of the pouch with first adhesive layer 30. Appropriate cutting means can then be employed to simultaneously form opening 38, opening 36, and access opening slit 22. The webs 12 and 14 can then be joined together, with heat sealing or like formation of end seal 18 being effected through a portion of the release paper 36 and adhesive structure 26.

The adhesive structure 26 preferably comprises a double-faced, pressure-sensitive adhesive tape, such as Scotch ™ adhesive transfer tape R-70, No. 464, marketed by 3M Industrial Specialties Division, St. Paul, Minn. In one current embodiment of the invention, a double-faced adhesive tape having an adhesive width of 0.75 inches has been used.

Significantly, the disclosed adhesive structure is adapted to provide tamper-indication (i.e., visual evidence of opening or attempted opening) in the event that access opening slit 22 is opened after sealing thereof. Specifically, the laminate adhesive structure 26 is configured such that the effective adhesive strength and cohesive strength of each of first and second adhesive layers 30 and 32 is greater than the cohesive strength of adhesive carrier member 28. Thus, after access slit 22 has been sealed with adhesive structure 26 and the adhesive of layer 32 has sufficiently set or cured (usually within several minutes of sealing, depending upon the quantity and type of adhesive, the sealing pressure, and temperature), any attempt to open the access slit results in delamination of the adhesive structure by rupture or destruction of carrier member 28, thereby providing a clear, visually discernible indication of tampering.

As noted, first adhesive layer 30 is adapted to secure adhesive structure 26 to first pouch 12 of pouch 10. In this regard, it can be desirable to subject the portion of first pouch web 12 which receives the adhesive structure 26 to corona discharge treatment shortly before adhesive structure 26 is affixed to first pouch web 12 with adhesive layer 30. Such treatment is particularly desirable when first pouch web 12 comprises polyolefin plastic film. Since the closing seal of the pouch is effected with an adhesive-to-adhesive interface, the pouch's useful shelf life is not dependent upon the freshness of any such corona discharge treatment.

In addition to providing tamper-indication, the provision of laminate adhesive structure 26 facilitates convenient and proper closing of the pouch 10. The adhesive carrier member 28, which as noted preferably comprises paper, desirably acts as a reinforcing member which stiffens the portion of pouch 10 folded onto itself, thus facilitating convenient manipulation for closing. This reinforcing or rigidification by the members 28 is particularly desirable when the pouch webs 12 and 14 comprise plastic film material since such material is usually flexible and non-rigid. This added benefit of the tamper-indicating laminate adhesive structure is significant in view of the importance of properly closing and sealing the present pouch when configured for sterilization or sterility maintenance use.

Closing and sealing of access opening slit 22 with laminate adhesive structure 26 is illustrated in FIG. 4. In this figure, pouch 10 is illustrated as folded onto itself about the natural folding line defined by access opening slit 22. This fold is effected after the contents of the pouch have been inserted therein, and release paper 36 removed. As is evident in FIG. 4, the adhesive-to-adhesive closing seal for the pouch is effected between the confronting surfaces of second adhesive layer 32, which is brought into confronting relation with itself when the pouch is folded. Because the adhesive of layers 30 and 32 is selected to have an effective adhesive strength and cohesive strength greater than the cohesive strength of adhesive carrier member 28, any attempts to gain access to the interior of the pouch via the sealed access slit 22 results in rupture of the adhesive carrier member 28, causing the adhesive structure to delaminate and thus clearly indicate tampering.

FIG. 5 illustrates a modification of the above-described laminate adhesive structure and associated release paper. In FIG. 5, a laminate adhesive structure 26' is provided, including an adhesive carrier member 28', and first and second pressure-sensitive adhesive layers 30' and 32'. The adhesive structure 26 defines an opening 34' aligned with access opening slit 22 defined by first pouch web 12. In this modified form, a removable release paper 36' is provided on the surface of second adhesive layer 32', with the release paper 36' defining a further opening 38' in alignment with access opening slit 22 and opening 34 in the adhesive structure. Notably, the laminate adhesive structure 26' and release paper 36' are dimensioned with respect to each other such that the release paper 36' is larger than the laminate adhesive structure 26'. By this construction, convenient removal of the release paper 36' is facilitated. For this type of adhesive construction, Scotch TM extended liner adhesive transfer tape R-70, No. 464XL, can be employed. Such a tape has an adhesive width of 0.75 inches, with a release paper of a 1.0 inch width.

Referring now to FIG. 6, an alternate embodiment of the present self-sealing pouch is disclosed. In this embodiment the arrangement for sealing the access opening slit 22 in first web 12 is provided by a pair of laminate adhesive structures 40 positioned on respective opposite sides of the access opening slit 22 on first web 12. Each laminate adhesive structure 40 can be appropriately provided by a strip of double-faced tape as described above, and thus each adhesive structure includes an adhesive carrier member 42 (preferably paper), and first and second pressure-sensitive adhesive layers 44 and 46 disposed on respective opposite sides of the adhesive carrier members 42. In this embodiment, closing and sealing of access opening slit 22 is effected by removing a release paper 48 provided on each of the second adhesive layers 42 of the laminate adhesive structures 40, with the pouch then folded onto itself so that the second adhesive layers 46 are brought into confronting relation to close the pouch with an adhesive-to-adhesive seal.

A further embodiment of the present pouch is illustrated in FIG. 7. In this embodiment, a single pressure-sensitive adhesive layer 50 is provided on first pouch web 12 in association with access opening slit 22, with the adhesive layer 50 defining an opening 52 aligned with the opening slit 22 of web 12. A removable release paper 54 is affixed to the outwardly facing surface of adhesive layer 50, with the pouch being sealable by removing release paper 54, and thereafter folding the pouch onto itself so that the adhesive layer 50 is brought into confronting relation with itself, thus forming an adhesive-to-adhesive closing seal.

FIG. 8 illustrates a modified form of the embodiment of the present pouch illustrated in FIG. 7. In the modification of FIG. 8, a single adhesive layer 50', defining an opening 52' aligned with access opening slit 22, is dimensioned with respect to a removable release paper 54' such that the release paper is larger than the adhesive layer 50'. Thus, convenient removal of the release paper is facilitated.

Referring now to FIG. 9, a further embodiment of the present pouch is illustrated. In this embodiment, a pair of strips of single layer pressure-sensitive adhesive 60 is provided such that each adhesive layer 60 is disposed on a respective opposite side of the access opening slit 22. Each adhesive layer 60 is provided with a release paper 62 to maintain the freshness of the adhesive, with sealing of the pouch being effected by folding the pouch about access opening slit 22 to bring the adhesive layers into confronting relation with each other.

As will be recognized from the foregoing, numerous variations and modifications may be effected without departing from the true spirit and scope of the concept of the present invention. For example, the present invention can be embodied as a self-sealing pouch wherein the pouch webs are marginally joined together, with the second of the webs extending beyond an unsealed end edge of the first pouch web, the first web thus defining the access opening to the interior of the pouch. In such a construction, the desired adhesive-to-adhesive closing seal can be achieved by providing pressure-sensitive adhesive means on the pouch webs such that the unsealed end of the first pouch web is flanked by adhesive. A pair of pressure-sensitive adhesive strips can be provided for this purpose, or a single adhesive strip can be employed, with openings defined by the adhesive strip and its release paper disposed in alignment with the unsealed edge of the first pouch web to permit insertion of articles into the pouch.

It will be understood that no limitation with respect to the specific constructions illustrated herein is intended or should be inferred. It is, of course, intended to cover by the appended claims all such modifications as fall within the scope of the claims.

What is claimed is:
1. A self-sealing pouch, comprising:
   first and second generally coextensive webs joined together along marginal edge portions thereof, said first web comprising plastic film material;
   an elongated access opening defined by said first web generally adjacent one end thereof for providing access to the interior of said pouch, said access opening extending generally transversely of said pouch; and pressure-sensitive adhesive sealing means provided on said first web on opposite sides of said access opening so that said opening can be sealed by folding said pouch to bring said adhesive means into confronting relation with itself to form an adhesive-to-adhesive seal for closing said access opening.

2. A self-sealing pouch in accordance with claim 1, wherein
said first and second webs are joined together by heat seal means along all marginal edge portions of plastic film said first and second webs.

3. A self-sealing pouch in accordance with claim 1, wherein
said first and second webs comprise a single piece of web material folded onto itself to provide said generally coextensive first and second webs, said first and second webs being joined at the fold of said piece of web material and being further joined together by heat seal means along the remaining marginal edge portions thereof.

4. A self-sealing pouch in accordance with claim 1, including
means apart from said access opening for opening said pouch after said access opening has been sealed.

5. A self-sealing pouch in accordance with claim 4, wherein
said means for opening said pouch comprises a tear notch defined by said joined together first and second webs on at least one marginal edge of said pouch intermediate the ends thereof.

6. A self-sealing pouch in accordance with claim 1, including
removable release paper means covering said adhesive sealing means, said release paper means being dimensioned larger than said adhesive sealing means.

7. A self-sealing pouch in accordance with claim 1, wherein
said adhesive sealing means comprises a pair of pressure-sensitive adhesive strip means provided on said first web on respective opposite sides of said elongated access opening.

8. A self-sealing pouch in accordance with claim 1, wherein
said adhesive sealing means comprises pressure-sensitive adhesive strip means on said first web defining an opening in alignment with said elongated access opening.

9. A self-sealing pouch in accordance with claim 8, including
removable release paper means covering said pressure-sensitive adhesive strip means, said release paper means defining a further opening in alignment with said elongated access opening.

10. A self-sealing pouch, comprising:
first and second, generally coextensive plastic film webs joined together along all marginal edge portions thereof;
access slit means defined by said first plastic film web generally adjacent one end thereof for providing access to the interior of said pouch, said access slit means extending generally transversely of said pouch; and pressure-sensitive adhesive means provided on said first plastic web in substantially adjacent relation to and on opposite sides of said access slit means so that said access slit means can be sealed by folding said pouch along a line defined by said access slit means to bring said pressure-sensitive adhesive means into confronting relation with itself to form an adhesive-to-adhesive seal.

11. A self-sealing pouch in accordance with claim 10, wherein
said first and second plastic film webs are joined together along opposite lateral marginal edge portions thereof by heat seal means, said access slit means extending transversely of said pouch less than the distance between the heat seal means joining together the opposite lateral marginal edge portions of said webs.

12. A self-sealing pouch in accordance with claim 10, including
means for opening said pouch after said access slit means has been sealed comprising a tear notch defined by said joined together plastic webs on at least one marginal edge of said pouch.

13. A self-sealing pouch in accordance with claim 12, wherein
said pressure-sensitive adhesive means comprises a single pressure-sensitive adhesive strip affixed to said first plastic film web and defining an opening in alignment with said access slit means,
said pouch including removable release paper means covering said pressure-sensitive adhesive strip, and defining a further opening in alignment with said access slit means.

14. A self-sealing pouch in accordance with claim 13, wherein
said release paper means is dimensioned larger than said pressure-sensitive adhesive strip to facilitate removal of said release paper means.

15. A self-sealing pouch in accordance with claim 13, wherein
said first and second plastic film webs each comprises a polyolefin plastic film, the portion of said first web to which said pressure-sensitive adhesive strip is affixed being corona discharge treated.

16. A self-sealing pouch, comprising:
first and second generally coextensive and rectangular pouch webs joined together along marginal edge portions thereof to define the interior of said pouch;
a transversely extending access opening slit defined by said first pouch web generally adjacent one end of said pouch for providing acess to the interior of the pouch;
pressure-sensitive adhesive means comprising a single pressure-sensitive adhesive strip provided on respective opposite sides of and about said transversely extending access opening slit for closing said slit by folding said pouch onto itself along a line defined by said access opening slit to bring said pressure-sensitive adhesive means into confronting relation with itself to form an adhesive-to-adhesive seal, said adhesive strip defining an opening in alignment with said access opening slit;
removable release paper means removably disposed on said pressure-sensitive adhesive means, said release paper means being removable from said adhesive means to permit closing of said access opening slit with said adhesive means, said release paper means defining another opening in alignment with said access opening slit; and means apart from said access opening slit for opening said pouch after said access opening slit has been closed.

17. A self-sealing pouch in accordance with claim 16, wherein said first and second pouch webs each comprises plastic film material, said means apart from said access opening slit for opening said pouch comprising a tear notch defined by the joined together respective lateral edge portions of said first and second plastic film pouch webs.

* * * * *

UNITED STATES PATENT AND TRADEMARK OFFICE
CERTIFICATE OF CORRECTION

PATENT NO. : 4,510,621

DATED : April 9, 1985

INVENTOR(S) : Dennis A. Sak and Thomas Mestetsky

It is certified that error appears in the above-identified patent and that said Letters Patent is hereby corrected as shown below:

In column 9, line 6, after the word "adhesive", insert the word --sealing--.
In column 9, line 14, delete the words "plastic film".
In column 9, line 18, before the word "web" insert the words --plastic film--.
In column 10, line 52, the word "acess" should be "access".

Signed and Sealed this

Thirtieth Day of July 1985

[SEAL]

Attest:

DONALD J. QUIGG

Attesting Officer     Acting Commissioner of Patents and Trademarks